United States Patent [19] [11] 4,012,508
Burton [45] Mar. 15, 1977

[54] TOPICAL COMPOSITION AND METHOD
[76] Inventor: Verna M. Burton, 1223 Lincoln Road, Rte. 7, Allegan, Mich. 49010
[22] Filed: Feb. 3, 1975
[21] Appl. No.: 546,813
[52] U.S. Cl. .............................. 424/235; 424/240
[51] Int. Cl.$^2$ ................ A61K 31/605; A61K 31/56
[58] Field of Search ........................... 424/235, 240

[56] References Cited
OTHER PUBLICATIONS
Heliane et al., Chem. Abst., vol. 77 (1972) p. 105,596t.
Physicians' Desk Reference, 28th edit. (1974) p. 1017.
New Drugs, 1965 Edition (AMA) pp. 311–315.

*Primary Examiner*—Sam Rosen
*Attorney, Agent, or Firm*—McGarry & Waters

[57] ABSTRACT

An ointment for topical use comprising a small amount of a cortical steroid intimately mixed with aspirin in a suitable carrier such as petroleum jelly wherein about 45 to 125 parts of the steroid per million parts of the aspirin are present in the mixture. The ointment is applied to corns, calluses, planter's and seed warts and other forms of skin disorders, preferably after soaking to remove the dematosis.

18 Claims, No Drawings

TOPICAL COMPOSITION AND METHOD

BACKGROUND OF THE INVENTION

1. Field of the Invention

This invention relates to compositions for treatment of skin disorders such as corns, warts, calluses and athlete's foot. In one of its aspects the invention relates to a method for treating skin disorders.

2. State of the Prior Art

Corns, warts and other similar skin disorders have plagued people of all types and occupations. These skin disorders are especially painful for those who must be on their feet extensively throughout the day. Many ointments have been developed to treat these skin disorders over the years, but no ointment has found to be especially effective for all types of problems.

The most extensively used composition is an ointment containing salicyclic acid in an oil carrier. This composition, although it works with inconsistent results, is very irritable to the skin and on occasion produces painful sores before removing the corns, warts and the like. As a result, the ointment is not used on diabetics.

SUMMARY OF INVENTION

A new composition which can be used on all types of patients has now been discovered for removing corns, warts and healing other skin disorders without producing sores or skin irritations. The composition comprises a small amount of a cortical steroid intimately mixed with aspirin and contained in a petroleum jelly or other suitable carrier for topical application.

The cortical steroids are those compositions generally described in the patent to Lerner U.S. Pat. No. 3,449,494, which is incorporated herewith by reference. Generally, the cortical steroid contemplated for use in the invention are compounds generally characterized as the cortisols, cortisones, corticosterones, cortexones, cortexalones, cortols, B-cortols, corto-lenes, B-cortolones, Tetrahydro E, Tetrahydro F, prednisolones, prednisones, triamcinolones, dexamethasones and the derivatives thereof possessing, concurrently, anti-inflammatory properties and glacocorticoidal activity, for example, the 6, -16, -21, -11, -9- or 2-substituted derivatives. Many of the steroids which may be satisfactorily employed in the practice of this invention are described by Sarrett et al, in their article, "The Effects of Structural Alteration on the Anti-Inflammatory Properties of Hydrocortisone," in Volume 5 of Progress in Drug Research (1963) pages 13, et seq.

The preferred cortical steroids are cortisone, betamethesone (valerate 9 fluora 11B, 17, 21 trihydroxy 16B methylpregna), methylprednisolone acetate and triamcinolone acetonide.

Aspirin (acetylsalicyclic acid) is well known and is commonly sold in tablet form. However, pure aspirin is far more desirable in the practice of the invention.

The carrier is any suitable material for the cortical steroid and the aspirin for topical application and includes oils, creams and petroleum jellies. Examples are baby oils, cold creams and petroleum jelly. Petroleum jelly is preferred.

The cortical steroid is used in small amounts with respect to the amount of aspirin. Generally, about 45 to 125 weight parts of the cortical steroid, preferably 55 to 95 weight parts of the cortical steroid, is intimately mixed with a million weight parts of aspirin.

The amount of the carrier with respect to the mixture can vary. A sufficient amount of carrier is required to provide a suitable medium for handling the cortical steroid and aspirin mixture and to serve as a vehicle for spreading the mixture evenly onto the areas to be treated. Generally, about 5 to 20 parts by weight of the mixture will be used with 100 parts of the carrier. The mixture can be even in lesser amounts when the composition is used on diabetics.

The composition of the invention has been found to be effective in treating planter's warts, corns, calluses, athlete's foot, ringworm, cold sores, chapped lips, infections and other skin disorders. Generally, the affected area is soaked in a hot liquid such as water prior to or intermittent to application of the ointment. In the case of athlete's foot, the liquid preferably contains vinegar. If desired, the affected areas can be treated without soaking for 4 to 5 days. Thereafter the soaking can commence prior to treatment.

The invention will now be illustrated with reference to the following examples.

EXAMPLE 1

Approximately 5 grams of Valisone was intimately mixed with 250 five-grain tablets (80 gms.) of pure aspirin and the mixture was combined with 2½ ounces of Vasoline. Valisone is an ointment commercially sold and the 5-gram sample contained about 6 mg. of beta methasone. The resulting composition had about 75 weight parts beta methosone per million weight parts of aspirin.

EXAMPLE 2

The ointment produced in Example 1 was applied to planter's warts on a person's foot. The application of the ointment was preceded by soaking the affected area in hot water for fifteen to twenty minutes. After the ointment was applied, it was covered with a bandage. After about four days the tissue started loosening up. The wart dropped off within seven days. After a few more days, the skin healed completely. No soreness was noted during the treated period.

EXAMPLE 3

The composition of Example 1 was applied to corns and the same procedure was followed as Example 2. Within seven days, the corns fell off leaving a hole in the skin which healed within a couple of days. The treatment of this example took place without any soreness to the affected area.

EXAMPLE 4

The composition of Example 1 was applied to calluses on a person's foot. The same procedure as Example 2 was also followed. The calluses were removed within seven days without any soreness to the affected area.

EXAMPLE 5

The composition of Example 1 was applied to seed warts. The composition was applied to the foot without soaking. The warts fell off within seven days.

EXAMPLE 6

The composition of Example 1 was applied to a portion of a person's foot having athlete's foot. The ointment was applied to the feet after soaking in a white vinegar water for fifteen to twenty minutes. In eight to ten days the athlete's foot disappeared and did not return.

EXAMPLE 7

The composition of Example 1 was applied to an area of a skin affected by exzema after cleansing the area thoroughly. In from one to two weeks the exzema cleared up.

EXAMPLE 8

The composition of Example 1 was prepared except that an equivalent amount of buffered aspirin was substituted for the aspirin. The composition was applied to corns on a person's foot. The same procedure as Example 2 was followed with soaking in hot water preceding the application of the ointment. After three weeks there was no apparent results and the corns were the same.

EXAMPLE 9

Five grams of Valisone was mixed with 2½ ounces of Vasoline to make an ointment. This ointment was applied to calluses and the procedure followed in Example 2 was followed with the affected area being soaked in hot water for fifteen to twenty minutes before application of the ointment. After three weeks there were no visible results to the treatment of the calluses. The calluses remained but were not quite as sore as they were prior to the treatment. The same ointment of this example was applied to planter's warts and the same procedure was followed, namely soaking before application of the ointment. After three weeks no apparent results were evident and the planter's warts remained.

EXAMPLE 10

The composition of Example 1 was mixed without the Valisone. This composition was applied to corns following the same procedure as Example 2, namely soaking before application of the ointment. After six days of this treatment, the skin appeared to be loose but the corns remained and the affected area was so sore that treatment could not be continued.

EXAMPLE 11

A commercial compound of Dr. Scholl's ointment No. 2331 for the treatment of calluses and planter's warts was tested on corns and calluses. This ointment contains salicyclic acid. This ointment was applied to calluses and planter's warts in the manner described above in Example 2. After a three-week period of time it was found to be ineffective.

EXAMPLE 12

About ½ oz. of the Dr. Scholl's ointment No. 2331 corn salve for removing corns and calluses was mixed with 5 grams of Valisone. This ointment was applied to corns for five days without soaking. A soreness developed and the treatment could not be continued.

Subsequently, ointment prepared in accordance with Example 1 was applied to the corns and the procedure of Example 2 was followed. The corn cleared up within about seven days.

EXAMPLE 13

The composition of Example 1 was made except that 7.5 grams of Neo-Medral Acetate was substituted for Valisone. The composition was applied to corns in the same manner as Example 2 and found to be equally as effective as the composition of Example 1. Neo-Medral Acetate is a prescription ointment sold by the Upjohn Company and contains 0.1% methylprednisolone acetate and 0.5% neomycinsulfate in a petroleum jelly base.

EXAMPLE 14

The composition of Example 1 was made except that 5 grams of Kenalog ointment was substituted for the Valisone. Kenalog is a prescription ointment sold by Squibb and contains 0.1 percent triamcinolone acetonide in a mineral oil base. The composition was applied to corns as in Example 2 and found to be as effective as the composition of Example 1.

The foregoing examples show that the composition of the invention is very effective in healing skin disorders such as corns, calluses, athlete's foot, warts and the like. Compositions of the prior art including salicyclic acid compositions and the compositions including equivalent amounts of the ingredients by themselves do not produce satisfactory results.

Reasonable variation and modification are possible within the scope of the foregoing disclosure without departing from the spirit of the invention which is defined by the claims. For example, whereas the method of the invention contemplates the soaking of the affected area prior to application of the ointment, the soaking may take place other than directly before application of the ointment. For example, the soaking can take place in the morning and the application can be made at night. In addition, the soaking may be commenced after four to five days of application of the ointment without soaking.

The embodiments of the invention in which an exclusive property or privilege is claimed are defined as follows:

1. A composition for topical use in treatment of corns, warts, and athlete's foot, the composition comprising an effective amount of a cortical steroid intimately mixed with an effective amount of aspirin, and a carrier of oils, creams or jellies, wherein the relative proportion of aspirin is substantially greater than the portion of the cortical steroid in the composition.

2. A composition according to claim 1 wherein the said cortical steroid is a cortisone, betamethasone, methylprednisolone acetate or triamcinolone acetonide.

3. A composition according to claim 2 wherein about 45 to 125 weight parts of said cortical steroid is mixed with about one million weight parts of aspirin.

4. A composition according to claim 2 wherein about 55 to 95 weight parts of the cortical steroid is mixed with about one million weight parts of aspirin.

5. A composition according to claim 1 wherein about 45 to 125 weight parts of the cortical steroid is mixed with about one million weight parts of the aspirin.

6. A composition according to claim 1 wherein about 55 to 95 weight parts of the cortical steroid is mixed with about one million weight parts of aspirin.

7. A composition according to claim 1 wherein the carrier is petroleum jelly.

8. A composition according to claim 1 wherein the cortical steroid is a cortisone, about 75 weight parts of the cortical steroid is mixed with about one million weight parts by way of aspirin, and the carrier is a petroleum jelly.

9. A method of treating a skin disorder comprising applying to the affected area an effective amount of a composition comprising a small amount of a cortical steroid intimately mixed with a relatively large amount of aspirin and a carrier of oils, creams or jellies.

10. A method for treating a skin disorder according to claim 9 wherein said cortical steroid is a cortisone, betamethesone, methylprednisolone acetate or triamcinolone acetonide.

11. A method for treating a skin disorder according to claim 10 wherein about 45 to 125 weight parts of the cortical steroid is intimately mixed with about one million weight parts of the aspirin.

12. A method for treating skin disorders according to claim 10 wherein about 75 weight parts of the cortical steroid is mixed with about one million weight parts of aspirin.

13. A method for treating skin disorders according to claim 12 wherein the carrier is petroleum jelly.

14. A method for treating skin disorders according to claim 13 wherein the application of the composition is preceded by soaking the affected skin area in hot water.

15. A method for treating a skin disorder according to claim 9 wherein the application of the composition is preceded by soaking the affected area in hot water.

16. A method for treating a skin disorder according to claim 9 wherein the skin disorder is a wart.

17. A method of treating a skin disorder according to claim 9 wherein the skin disorder is a corn.

18. A method of treating a skin disorder according to claim 9 wherein the skin disorder is athlete's foot.

* * * * *